(12) United States Patent
Turchetta et al.

(10) Patent No.: US 9,308,174 B2
(45) Date of Patent: Apr. 12, 2016

(54) LYOPHILIZED FORMULATIONS OF BENDAMUSTINE HYDROCHLORIDE

(71) Applicant: CHEMI S.P.A., Cinisello Balsamo (IT)

(72) Inventors: Stefano Turchetta, Patrica (IT); Maurizio Zenoni, Patrica (IT); Paolo Brandi, Patrica (IT)

(73) Assignee: CHEMI S.P.A., Cinisello Balsamo (IT)

( * ) Notice: Subject to any disclaimer, the term of this patent is extended or adjusted under 35 U.S.C. 154(b) by 0 days.

(21) Appl. No.: 14/306,316

(22) Filed: Jun. 17, 2014

(65) Prior Publication Data

US 2014/0378518 A1    Dec. 25, 2014

(30) Foreign Application Priority Data

Jun. 19, 2013 (IT) .............................. MI2013A1013

(51) Int. Cl.
| | | |
|---|---|---|
| A61K 9/19 | (2006.01) | |
| A61K 31/4184 | (2006.01) | |
| A61K 9/00 | (2006.01) | |
| A61K 47/26 | (2006.01) | |

(52) U.S. Cl.
CPC ................ *A61K 9/19* (2013.01); *A61K 9/0019* (2013.01); *A61K 31/4184* (2013.01); *A61K 47/26* (2013.01)

(58) Field of Classification Search
USPC ....................................... 514/394
See application file for complete search history.

(56) References Cited

U.S. PATENT DOCUMENTS

| | | |
|---|---|---|
| 8,436,190 B2 | 5/2013 | Brittain et al. |
| 8,461,350 B2 | 6/2013 | Brittain et al. |
| 8,609,863 B2 | 12/2013 | Brittain et al. |
| 8,791,270 B2 | 7/2014 | Brittain et al. |
| 8,895,756 B2 | 11/2014 | Brittain et al. |
| 2006/0159713 A1 | 7/2006 | Brittain et al. |
| 2014/0080880 A1 | 3/2014 | Toti et al. |

FOREIGN PATENT DOCUMENTS

| | | |
|---|---|---|
| CN | 101584668 | 11/2009 |
| CN | 101836962 | 9/2010 |
| CN | 101966158 | 2/2011 |
| CN | 103860482 | 6/2014 |
| DE | 159289 | 3/1983 |
| EP | 2574334 | 4/2013 |
| WO | WO2006076620 | 7/2006 |
| WO | WO2012103226 | 8/2012 |

OTHER PUBLICATIONS

Search Report and Written Opinion of PCT/EP2014/062618 of Oct. 9, 2014, mailed on Nov. 27, 2014.
Ozegowski et al," ••[Bis•(Rchlorathyl)•amino•benzimidazolyl•(2)]•propion• bzw.•buttersauren als potentielle Cytostatika" Journal Fur Praktische Chemie. 4 (20) 178:186 (1963).
Maas et al., "Stabilitat von Bendamustinhydrochlorid in Infusionslosungen", Pharmazie, 49 (10) 775-777 (1994).

*Primary Examiner* — Kristin Vajda
(74) *Attorney, Agent, or Firm* — Silvia Salvadori, P.C.; Silvia Salvadori

(57) ABSTRACT

New formulations of bendamustine hydrochloride having HPLC purity higher than 99% obtained through the lyophilization of aqueous solutions without organic solvents, are described.

15 Claims, 8 Drawing Sheets

Bendamustine impurities

Bendamustine Ethyl ester impurity

Bendamustine Dimer trichloride impurity

Bendamustine HP1 impurity

Bendamustine Dimer trihydroxy impurity

LYOPHILIZED FORMULATIONS OF BENDAMUSTINE HYDROCHLORIDE

This application is a Non-provisional application which claims priority to and the benefit of Italian Application No. MI2013A001013 filed on Jun. 19, 2013, the content of which is incorporated herein by reference in its entirety.

The present invention relates to new lyophilized formulations of bendamustine hydrochloride and, more particularly, to lyophilized formulations of bendamustine hydrochloride obtained from aqueous solutions devoid of organic solvents, having HPLC purity higher than 99%.

STATE OF THE ART

Bendamustine hydrochloride is an active ingredient which is used in the treatment of chronic lymphocytic leukemia and non-Hodgkin's lymphoma, whose chemical structure is represented by the following formula I.

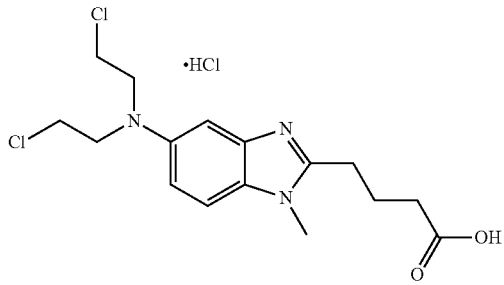

This drug belongs to the class of nitrogen mustards and acts as anti-tumoral agent thank to the active part of the molecule constituted by the bis-chloroethylamino group, that under physiological conditions forms, through an internal replacement of the amino nitrogen on one of the two chlorine atoms, a highly reactive and electrophilic aziridine-type structure that is able to effectively react with the nitrogen bases of the nucleic acids causing serious changes of cellular replication and reparation that lead to apoptosis.

The active ingredient is commercially available in the form of lyophilized powder under the trade name Treanda® in the USA and Levact® in Europe, in dosages of 25 mg and 100 mg.

The synthesis of bendamustine was reported for the first time in W. Ozegowski, D. Krebs, *Journal Für Praktische Chemie*, 4 (20) 178-186 (1963).

DD159289 discloses that the lyophilization of bendamustine from an aqueous solution or from an aqueous solution containing sodium chloride gives extremely hygroscopic lyophilized products characterized by a remarkable degradation of the active ingredient (from 5% to 10%). Furthermore, the document discloses that after the reconstitution of the product lyophilized from water, microparticles are formed contributing to the instability of the system. In the document it is observed that a way to overcome the disadvantage of the hygroscopicity of the lyophilized product seems to be represented by the addition of mannitol to the mixture to be lyophilized; however it is reported that such addition does not solve the problem of the remarkable decomposition of the active ingredient and the formation of microparticles after reconstitution.

The paper B. Maas, C. Huber, I. Krämer, *Pharmazie*, 49 (10), 775-777 (1994) discloses data confirming the instable behavior of bendamustine in aqueous solution: an aqueous solution of bendamustine hydrochloride with a concentration of 0.25 mg/ml has a 10% degradation of the active ingredient after 4.2 hours at room temperature. Such instability increases with the increasing of the temperature: at 4° C. the time needed for the solution of bendamustine hydrochloride to lose 10% of its title ($t_{90}$) is 119.5 hours, while at 23° C. such $t_{90}$ is only 9.2 hours. The paper also discloses the mechanism of the formation of the main degradation product of bendamustine in water, named HP1, which is generated according to the mechanism reported in the following scheme 1.

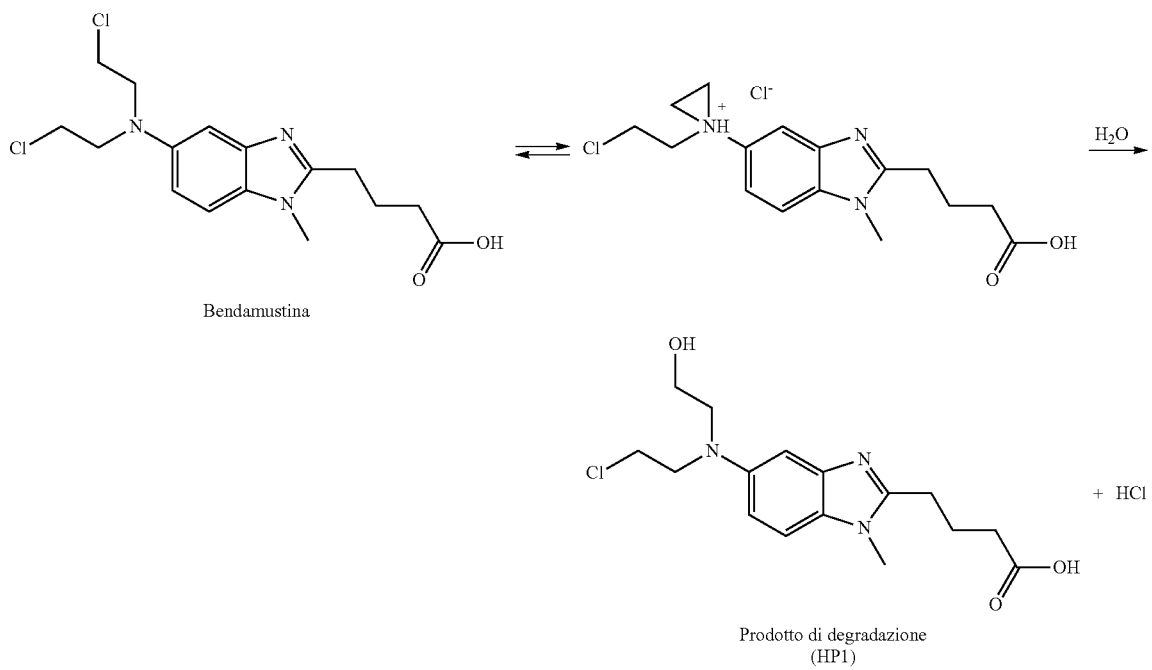

The same paper also discloses the inhibition effect exerted by sodium chloride on the degradation of the active ingredient in aqueous solution.

WO2006076620 discloses the preparation of lyophilized products of bendamustine obtained by using mixtures of water and organic solvents such as t-butanol, ethanol, n-propanol, n-butanol, isopropanol, methanol, acetone, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, hexafluoroacetone, chlorobutanol, dimethyl sulfone, acetic acid and cyclohexane. In the document there are reported data according to which the use of organic solvents and water significantly contributes to the stabilization of the active ingredient and to the obtainment of a lyophilized product with a low content of impurities, especially of HP1 impurity. The document however does not report any data about the content of residual solvents remaining in the products after the lyophilization. Furthermore, the use of an organic solvent in the mixture to be lyophilized necessarily involves the use of suitable lyophilizers that are able to operate with organic solvents, with the consequent increase of the production costs.

The data reported in WO2006076620 advice against the lyophilization of bendamustine hydrochloride from sole water. It is indeed disclosed the preparation of a solution of bendamustine hydrochloride (15 mg/ml) and mannitol (25.5 mg/ml) in sole water, cooled at 5° C. (page 28, line 7 and table 1). About this solution, it is reported that after 6 hours there is the formation of a precipitate, showing the low solubility of bendamustine hydrochloride in water.

Furthermore, samples of the same solution, analyzed by HPLC after 0, 3, 6, 24 hours (page 30, lines 16-20 and table 3; page 43, lines 4-9) show that bendamustine quickly degrades in water, by predominantly forming the HP1 degradation product. In detail, at time=0, the HP1 percentage is 0.6%, after 3 hours it increases to 0.86% and reaches the value of 3.81% after 6 hours.

In said document it is also pointed out (page 44, lines 22-24) that at least 134 mg/vial of mannitol should be used for the 100 mg dosage of active ingredient to obtain well formed lyophilized products resistant to cracking, with no differences observed when amounts of mannitol up to 200 mg/vial are used.

However, high amounts of mannitol in the vial to be lyophilized increase the possibilities of vial breakages during the lyophilization, due to uncontrolled phase transitions of mannitol (see for example "Mechanistic studies of glass breakage for frozen formulations. I and II. Vial breakage caused by crystallizable excipient mannitol" in *J. Pharm. Sci. Technol.* 2007 November-December; 61(6): 441-51 and 452-60). The possibility that a vial of a cytotoxic active ingredient could break during the lyophilization represents a particularly undesired feature from the safety point of view.

CN101836962 discloses the lyophilization of bendamustine hydrochloride from solutions using water as sole solvent. The method described in this patent application includes firstly the dissolution of the active ingredient and the excipient at a temperature from 30° C. to 50° C., then the cooling of the mixture to 0-10° C., the adjustment of the pH from 2.0 to 3.0, the treatment with active charcoal, the filtration, the filling of the vials and the lyophilization. The treatment of the active ingredient in warm conditions in the first steps of the process inevitably causes the degradation of said active, as shown by the data reported in the cited patent application where the lyophilized product prepared according to the disclosed method has an overall impurity content of 1.85%.

Moreover, the examples reported in the cited patent application do not define the concentrations and the times needed to prepare the described lyophilized products.

CN101966158 discloses a process for the preparation of lyophilized formulations of bendamustine hydrochloride in which no organic solvents are used. The dissolution of the excipients and of the active ingredient is carried out from 0 to 20° C. at concentrations of the active from 1 mg/ml to 100 mg/ml, the pH is adjusted from 1.5 to 4.5, the solution is filtered for depyrogenation, put into vials and lyophilized. This document does not report information about the purity of the obtained lyophilized products, but only about their assay in active ingredient without providing details about the obtainment of said assay. The data reported in this document show a complete lack of correlation between the assay of the obtained lyophilized products and the temperature at which they are prepared. This is in contrast with what it is known in the literature about the stability in water of bendamustine (see the aforementioned Pharmazie 1994): the greater the stability of bendamustine in water, the lower the temperature at which it is maintained.

WO2012103226 discloses the lyophilization of bendamustine hydrochloride using mixtures of solvents, such as acetone and acetonitrile, and water; from these mixtures, lyophilized products with high purity (wherein HP1 does not exceed 0.24%) stable at 25° C. and 40° C. at least for 3 months and that reconstitute in about 1 minute, are obtained.

However, also this document does not report the amount of the organic solvent that is present as residual solvent in the lyophilized product and also in this case the use of the organic solvent in the mixture to be lyophilized requires suitable equipments with higher production costs with respect to the use of lyophilizers from sole water.

The commercial products Levact® and Treanda® are presumably prepared by lyophilization from mixtures of organic solvents and water according to one of the methods known in the literature, since the analysis carried out by the present Applicant on such products show the presence of residual organic solvents.

US2014080880 describes the preparation of lyophilized bendamustine hydrochloride from solutions that do not contain organic solvents. In all the examples described in this patent application it is used a ratio API:mannitol equal to 15:25.5, and it is used a quantity of mannitol/vial for the dosage of 100 mg of active ingredient equal to 170 mg.

A high quantity of mannitol increases the possibility of having undesirable events, especially from the point of view of safety, such as breaking of the vials during lyophilization (see references at pages 4-5) and lowers the solubility of the active principle in the pre-lyophilization solution, increasing the possibility that this precipitates before freezing, giving a lyophilisate of poor quality.

Therefore, there is still the need to find a method, easily to be industrialized, to lyophilize bendamustine hydrochloride at low cost, that is able to produce a lyophilized product with a low content of impurities, that reconstitutes within a minute, that does not contain organic solvents, that is stable on time and that show a negligible risk of vial breakage during the lyophilization.

OBJECT OF THE INVENTION

We have now surprisingly found that bendamustine hydrochloride can be lyophilized from sole water, without the need of organic solvents, while keeping the percentage of degradation products below 1% and implementing a safe scalable industrial process.

Therefore object of the present invention is a safe industrial process to prepare lyophilized products of bendamustine hydrochloride from solutions containing sole water as a solvent, having HPLC purity higher than 99%.

A further object of the present invention are lyophilized formulations of bendamustine hydrochloride with purity >99% devoid of residual organic solvents, obtained by the process of the present invention.

The process object of the present invention allows to carry out all the necessary steps to obtain the pre-lyophilization solution (mixing, dissolution, sterile filtration and distribution in vials) without the contemporary formation of degradation products in an amount higher than 1% and, more specifically not higher than 0.5% and to obtain then a lyophilized product that reconstitutes in few minutes without the formation of insoluble material.

This result is particularly unexpected in view of the prior art that clearly advices the person skilled in the art against any attempts to lyophilize bendamustine hydrochloride without using organic solvents, as the product easily degrades by dissolving it in sole water. Moreover, the process described in the present patent application represents the base for a particularly advantageous industrial process as it does not provide the use of any organic solvent, shows reduced risks of vial breakage due to uncontrolled crystallization of mannitol during the lyophilization, and allows to obtain the lyophilized product with a HPLC purity higher than 99%.

DETAILED DESCRIPTION OF THE INVENTION

In contrast with what is reported in the prior art, we have surprisingly found that bendamustine hydrochloride can be lyophilized from solutions in sole water without causing the formation of degradation impurities in amounts higher than 1%. Such result is achieved by using special arrangements in the steps of pre-lyophilization and mixing of the active ingredient with the excipients and water and by using reduced amounts of mannitol in comparison to the prior art.

Particularly the temperature in the various steps for the preparation of the solution to be lyophilized and the concentrations of the active ingredient and of the excipients have to be strictly controlled. In fact, even if from one side higher temperatures increase the solubility of the active ingredient, from the other side they cause its faster degradation with the consequent formation of considerable amounts of by-products.

Therefore, the lyophilization process object of the present invention comprises in a first phase the dissolution of bendamustine hydrochloride in water at a concentration from 15 to 4 mg/ml, at a temperature from 0° C. to 15° C.

Generally, the complete dissolution is obtained after 5-10 minutes at said temperature.

The resultant solution of bendamustine hydrochloride is added to an aqueous solution of the remaining excipients at a concentration from 15 to 10 mg/ml, pre-cooled at a temperature from −5° C. to +5° C.

Alternatively, the process foresees the preliminary preparation of a solution of water and excipients at a concentration of between 8.5 and 4.3 mg/ml kept at a temperature from 0 to 5° C. and the addition of bendamustine hydrochloride in a sufficient amount to achieve a final concentration of the active ingredient in solution from 5.5 to 2.0 mg/ml.

The resultant pre-lyophilization solutions, containing a concentration of the active ingredient from 5.5 to 2.0 mg/ml and a concentration of excipients from 8.5 to 3.0 mg/ml, are kept at a temperature not higher than 5° C., preferably from 0° C. to 4° C. and maintain a high purity degree, higher than 99% for at least three hours, allowing the accomplishment of all the phases preliminary to the lyophilization process, such as for example the sterile filtration of the solution, the filling of the vials and their insertion in the lyophilizer before cooling, also in an industrial scale preparation.

The process object of the present invention does not also require any pH adjustment in any of its phases and does not provide treatments with active charcoal.

The excipients that are used for the preparation of the aqueous solution to be added to the aqueous solution of bendamustine hydrochloride according to the lyophilization process, object of the present invention, are excipients conventionally used for the preparation of lyophilized products.

Particularly, bulking agents such as mannitol, lactose, sucrose and their mixtures are used.

Mannitol is particularly preferred. Still more preferably, the weight amount of mannitol is about 120% with respect to the weight of bendamustine hydrochloride.

The lyophilized product of bendamustine hydrochloride object of the present invention can contain also a stabilizing amount of NaCl.

When present, NaCl is added to the aqueous solution of the excipients and stabilizes the pre-lyophilization solution that is obtained after the addition of the aqueous solution of bendamustine hydrochloride to the suitably cooled aqueous solution of the excipients.

For an effective stabilization, the concentration of NaCl in the pre-lyophilization solution is preferably from 0.1% to 0.5% w/v.

The subsequent lyophilization of the pre-lyophilization solution obtained with the process of the present invention allows to obtain lyophilized bendamustine hydrochloride with a purity >99% and devoid of residual organic solvents, with the additional advantage that the lower amounts of mannitol which can be used substantially reduce the safety problems due to the accidental breakage of the vials during the lyophilization.

In the present context the absence of residual organic solvents in the lyophilized product means that the content of residual organic solvents is from 0 ppm to 10 ppm.

It is evident to the person skilled in the art that the purity degree of an active ingredient in lyophilized products depends on the purity degree of the used raw material.

In the specific case of bendamustine, the purity degree particularly depends on the lyophilization process used, due to the inherent instability of the molecule in water. By using bendamustine hydrochloride with a purity degree higher than 99%, as starting active ingredient, the purity degree of bendamustine hydrochloride in the lyophilized product of the present invention, evaluated by HPLC, remains substantially unchanged.

Preferably, the lyophilized product obtained from an aqueous solution according to the process of the present invention has a purity higher than 99.5%.

Moreover, the lyophilized products obtained with the process object of the present invention can be reconstituted in less than a minute resulting in clear and colorless solutions suitable for injectable preparations. Such lyophilized products are also stable under the standard conditions of the accelerated stability test.

In order to better illustrate the present invention without limiting it, the following examples are now given.

Example 1

Figure 1:
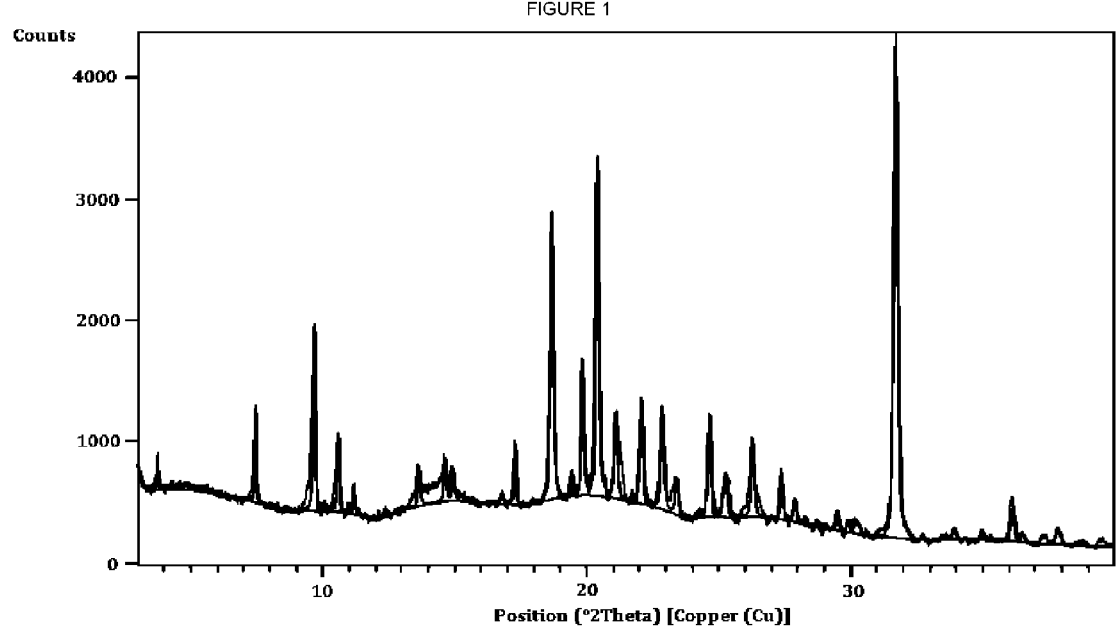
FIG. 1: PXRD of the product obtained in the example 2.

HPLC Method for the Determination of the Purity of Bendamustine Hydrochloride Solutions Operative Conditions
Instrument: HPLC SHIMADZU LC-10AD or equivalent
  UV Detector: SPD 10AVP or equivalent
  auto-sampler: SIL-ADVP or equivalent
Wavelength: 254 nm
Column: Kinetex 2.6μ XB-C18
  length: 150 mm
  I.D.: 4.6 mm
  Particle size: 2.6 μm
  (Phenomenex, Part. N. 00F-4496-Eo or equivalent)
Injection: 3 μL
Column temperature: 35° C.±1° C.
Sampler temperature: RT
Flow rate: 1.2±0.2 mL/min
Mobile phase: Eluent A: 0.1% $CF_3CO_2H$ in water
  Eluent B: 0.1% $CF_3CO_2H$ in acetonitrile
  Gradient mode
Analysis time: 20 minutes
Eluent A: 0.1% $CF_3CO_2H$ in water for HPLC
Eluent B: 0.1% v/v $CF_3CO_2H$ in acetonitrile for gradients.
Diluent: DMSO
Blank: use the diluent as blank
Gradient Program

| GRADIENT PROGRAM | | |
|---|---|---|
| Time (min) | Eluent A % (v/v) | Eluent B % (v/v) |
| 0 | 95 | 5 |
| 5 | 95 | 5 |
| 40 | 20 | 80 |
| 41 | 95 | 5 |
| 50 (run end) | 95 | 5 |

Preparation of the Samples:
Pre-Lyophilization Solutions.
  850 μL of diluent were taken with a 1000 μL calibrated micro-pipette and charged in a 2 mL HPLC vial. 150 μL of sample solution were taken with a 200 μL calibrated micro-pipette and charged in the same vial. The mixture was stirred for a few seconds.
Sample of Bendamustine HCl API
  3-5 mg of bendamustine HCl API were weighed in a 8 mL glass vial with screw cap.
  5 mL of diluent were charged in the same vial. The mixture was stirred up to dissolution.
Sample of Lyophilized Bendamustine HCl (without NaCl)
  5-8 mg of lyophilized bendamustine HCl were weighed in a 8 mL glass vial with screw cap. 5 mL of diluent were charged in the same vial. The mixture was stirred up to dissolution.
Sample of Lyophilized Bendamustine HCl (with NaCl)
  8-12 mg of bendamustine HCl were weighed in a 8 mL glass vial with screw cap. 5 mL of diluent were charged in the same vial. The mixture was stirred up to dissolution.

Purity Calculation
  The percentage of each known and unknown impurity was calculated as percentage area by using the following formula (the blank peaks and the peaks with area <0.05% were ignored)

$$\% \text{ impurity} = \frac{A_{xc} * 100}{A_{tot}}$$

wherein:
$A_{xc}$: peak area of the impurity in the sample.
$A_{tot}$: total area of the peaks of the chromatogram.
and
purity (A %)=100−$\Sigma_i$Imp (i)
  The peak corresponding to bendamustine was eluted at 28 minutes±2.

Example 2

Preparation of a Lyophilized Formulation of Bendamustine Hydrochloride from Sole Water, with Sodium Chloride

| | Amount/vial | Mannitol:API ratio |
|---|---|---|
| API | 100 mg | 1.7 |
| Mannitol | 170 mg | |
| NaCl | 90 mg | |
| Pre-lyophilization solution volume | 30 ml | |

In a 25 ml flask, 170.0 mg mannitol, 90 mg sodium chloride and 15 ml MilliQ water were charged. The mixture was kept under stirring until complete dissolution of the solids and brought to a temperature between −1° C. and 2° C. In another 25 ml flask, 15 ml of MilliQ water were charged and after cooling to 4° C., 100.0 mg of bendamustine hydrochloride (BND-HCl) were added. After about 30 seconds the complete dissolution of the solid was observed. This solution of bendamustine was then added to the first solution containing the excipients and the combined solutions, and kept between −1° C. and 2° C., were filtered through a 0.22 μm filter and kept between −1° C. and 2° C. up to 3 hours by checking every hour the purity of the mixture by HPLC according to the method reported in example 1.
  The obtained results are reported in the following table:

| Time | HP1 (Area %) | BND-HCl (Area %) |
|---|---|---|
| 0 | 0.17% | 99.83% |
| 1 h | 0.20% | 99.80% |
| 2 h | 0.24% | 99.76% |
| 3 h | 0.27% | 99.73% |

At the end of the process the solution was frozen to −20° C. and lyophilized in a Christ Alpha 1-4 LSC lyophilizer under the following conditions:

| | Time (hours) | T Shelf (° C.) | T Cond (° C.) | P (mbar) |
|---|---|---|---|---|
| Main Drying | 64 | −14 | <−45° C. | 0.1 |
| Final Drying | 24 | 25 | <−45° C. | 0.1 |

The obtained lyophilized product was analyzed by HPLC purity and PXRD analysis.

For the PXRD characterization (Powder X Ray Diffraction) the experimental conditions reported below were used:

| | |
|---|---|
| Type of instrument: | X'Pert PRO PANalytical |
| Type of measurement | Single scan |
| Wavelenght measurement | Cu Kα1 |
| Material of the anode: | Cu |
| Voltage of the X ray tube: | 40 |
| Power of the X ray tube (mA): | 40 |
| Type of movement of the sample: | Rotation |
| Time of rotation of the sample (s): | 1.0 |
| Thickness of the filter (mm): | 0.020 |
| Material of the filter: | Ni |
| Detector's name: | X'Celerator |
| Type of detector: | RTMS detector |
| Scan axis: | Gonio |
| Scan range (°): | 3.0000-39.9987 |
| Width of the range of measurement (°): | 0.0167 |
| Nr. of points: | 2214 |
| Scan mode: | Continue |
| Counting time (s): | 12.700 |
| Application software: | X'Pert Data Collector vs. 2.2d |
| Control software of the instrument: | XPERT-PRO vs. 1.9B |
| Temperature | Room temperature |

The HPLC purity was 99.64% with HP1=0.36%, while the PXRD is reported in FIG. 1.

The lyophilized reconstituted with 40 ml of water for injectable solutions provided a clear and colorless solution in 1 minute.

Example 3

Preparation of a Lyophilized Formulation of Bendamustine Hydrochloride by Sole Water, without Sodium Chloride (API Concentration in the Pre-Lyophilization Solution Equal to 3.33 mg/Ml)

| | Amount/vial | Mannitol:API ratio |
|---|---|---|
| API | 100 mg | 1.7 |
| Mannitol | 170 mg | |
| NaCl | — | |
| Pre-lyophilization solution volume | 30 ml | |

In a 50 ml flask, 170.0 mg mannitol and 30 ml MilliQ water were charged. The mixture was kept under stirring until complete dissolution of the solid and brought to the temperature of 4° C. 100.0 mg of bendamustine hydrochloride were then added. After about 30 seconds the complete dissolution of the solid was observed. This solution was brought between −1° C. and 2° C., filtered on a 0.22 μm filter and kept between −1° C. and 2° C. for 3 hours, checking every hour the purity of the mixture according to the HPLC method reported in example 1.

The obtained results are reported in the following table

| Time | HP1 (Area %) | BND-HCl (Area %) |
|---|---|---|
| 0 | 0.17% | 99.83% |
| 1 h | 0.28% | 99.72% |
| 2 h | 0.32% | 99.68% |
| 3 h | 0.38% | 99.62% |

At the end of the process the solution was frozen at −20° C. and lyophilized under the conditions reported in example 2.

The obtained lyophilized product was analyzed by HPLC purity (see example 1) and PXRD analysis.

Figure 2:
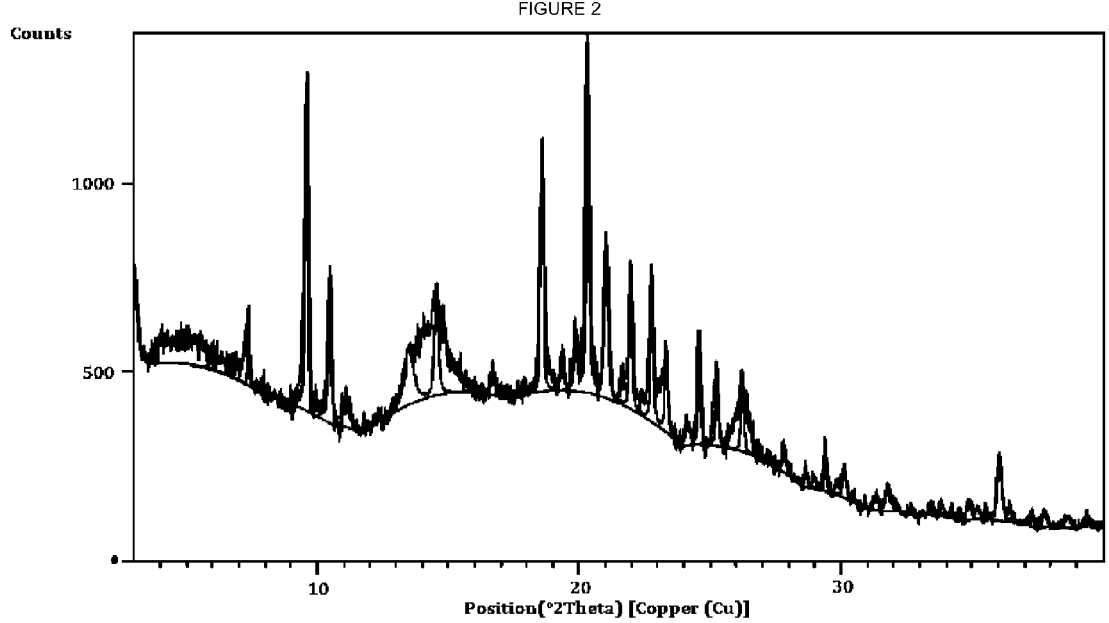
FIG. 2: PXRD of the product obtained in the example 3.

The HPLC purity was 99.51% with HP1=0.49%, while the PXRD is reported in FIG. 2.

The lyophilized product reconstituted with 40 ml of water for injectable solutions provided a clear and colorless solution in 1 minute.

Example 4

Stability of the Pre-Lyophilization Solutions of Bendamustine Hydrochloride

Table 2 reports the data of the variation of purity over the time of the mixtures obtained as reported in the previous examples, expressed in terms of formation of the HP1 impurity only, that is the only one to be formed in detectable amounts. The other two main known impurities, bendamustine dimer trichloride and bendamustine ethyl ester, were not found to be present in detectable amounts even if the used HPLC method was also validated for their evaluation.

All the preparations reported in table 2 were made by dissolving bendamustine hydrochloride (having HPLC purity 99.82% and HP1=0.14%) in the disclosed amount of milliQ water, at 12-14° C., keeping such mixture for 5-10 minutes under these conditions to ensure the complete dissolution and by adding such solution to the solution of mannitol and NaCl pre-cooled at 4° C. The resultant solution was then kept at 4° C. by monitoring over time the HPLC purity.

Table 2: Preliminary Data on the Preparation and Stability of Solutions of Bendamustine Hydrochloride in Water, Pre-Lyophilization.

Solution A

| BND-HCl solution | excipient solution |
|---|---|
| BND-HCl 100 mg | Mannitol 170 mg |
| H₂O 10 ml | NaCl 100 mg |
| | H₂O 10 ml |
| | (conc. NaCl 0.5% in 20 ml) |

| STABILITY | | |
|---|---|---|
| Time | impurity HP1 (area %) | Bendamustine (area %) |
| 0 | 0.17 | 99.83 |
| 1 h | 0.22 | 99.78 |
| 2 h | 0.24 | 99.76 |
| Appearance of the mixture after 2 hours: | | precipitate |

Solution B

| BND-HCl solution | excipient solution |
|---|---|
| BND-HCl 100 mg | Mannitol 170 mg |
| H₂O 10 ml | NaCl 220 mg |
| | H₂O 20 ml |
| | (conc. NaCl 0.75% in 30 ml) |

| STABILITY | | |
|---|---|---|
| Time | impurity HP1 (area %) | Bendamustine (area %) |
| 0 | 0.13 | 99.83 |
| 1 h | 0.26 | 99.78 |
| 2 h | 0.39 | 99.76 |
| Appearance of the mixture after 2 hours: | | strong opalescence |

Solution C

| BND-HCl solution | excipient solution |
|---|---|
| BND-HCl 100 mg<br>H₂O 10 ml | Mannitol 170 mg<br>NaCl 120 mg<br>H₂O 20 ml<br>(conc. NaCl 0.4% in 30 ml) |

| STABILITY | | |
|---|---|---|
| Time | impurity HP1 (area %) | Bendamustine (area %) |
| 0 | 0.13 | 99.83 |
| 1 h | 0.26 | 99.78 |
| 2 h | 0.39 | 99.76 |
| Appearance of the mixture after 2 hours: | | slight opalescence |

Solution D

| BND-HCl solution | excipients solution |
|---|---|
| BND-HCl 100 mg<br>H₂O 10 ml | Mannitol 170 mg<br>NaCl 90 mg<br>H₂O 20 ml<br>(conc. NaCl 0.3% in 30 ml) |

| STABILITY | | |
|---|---|---|
| Time | impurity HP1 (area %) | Bendamustine (area %) |
| 0 | 0.12 | 99.83 |
| 1 h | 0.16 | 99.78 |
| 2 h | 0.24 | 99.76 |
| Appearance of the mixture after 2 hours: | | clear |

Example 5

Preparation of a Lyophilized Formulation of Bendamustine Hydrochloride from Sole Water, without Sodium Chloride (API Concentration in the Pre-Lyophilization Solution Equal to 5 mg/Ml)

| | Amount/vial | Mannitol:API ratio |
|---|---|---|
| API | 100 mg | 1.7 |
| Mannitol | 170 mg | |
| NaCl | — | |
| Pre-lyophilization solution volume | 20 ml | |

In a 100 ml flask, 340.0 mg mannitol and 40 ml MilliQ water were charged. The mixture was kept under stirring up to a complete dissolution of the solid and brought to the temperature of 4° C. 200.0 mg of bendamustine hydrochloride (having 99.8% purity and 0.11% HP1 impurity) were then added. After about 5 minutes a complete dissolution of the solid was observed. This solution was brought to a temperature from −1° C. to 2° C. and kept under such conditions for 2 hours after which it was filtered on a 0.22 μm filter, frozen at −20° C. and lyophilized under the conditions reported in example 2. A lyophilized product having a content of water of 2.30%, measured with the Karl Fischer method, a HPLC purity 99.6% and HP1 impurity 0.29% was obtained.

Example 6

Preparation of a Batch of Vials Containing 25 mg of Active Ingredient

| | Amount/vial | Mannitol:API ratio |
|---|---|---|
| API | 25 mg | 1.7 |
| Mannitol | 42.5 mg | |
| NaCl | — | |
| Pre-lyophilization solution volume | 7.5 ml | |

In a 2 liter reactor, equipped with thermocryostat and mechanical stirring, cooled at 0° C. and coated with an aluminum sheet to shield the solution from light, a solution consisting of 5.66 g mannitol dissolved in 1 liter of water for injection was charged. Once the solution reached the thermal balance at 0-2° C., 3.34 g bendamustine hydrochloride (having 99.8% purity and 0.11% HP1 impurity) were added. A complete dissolution of the solid was obtained after about 30 seconds. The mixture was kept under stirring at 0-2° C. for 2 hours, then filtered and charged on a vial filling system. 100 dark-glass 20H vials were filled with 7.5 ml of such solution each, the vials were pre-capped with rubber stoppers for lyophilization and charged on a tray to be then transferred in a Minilyo Usifroid SMH45 lyophilizer with pre-cooled panels at 3° C.

A lyophilization cycle was applied according to the following table

| Lyophilization Cycle Shelves T | Set point (° C.) | Set Time (min) |
|---|---|---|
| Loading with pre-cooled shelves | +3° C. | For vials loading |
| Freezing (shelves cooling) | −45° C. | 96 |
| Freezing (shelves holding) | −45° C. | 180 |
| Annealing (shelves heating) | (0.5°/min) −10° C. | 70 |
| Annealing (shelves holding) | −10° C. | 180 |
| Annealing (shelves cooling) | (0.5°/min) −45° C. | 70 |
| Annealing (shelves holding) | −45° C. | 240 |
| Primary drying (shelves heating) | −20° C. | 250 |
| Primary drying (shelves holding) | −20° C. | 1440 |
| Primary Drying chamber pressure set point: 100 microbar | | |
| Secondary drying (shelves heating) | +25° C. | 225 |
| Secondary drying (shelves holding) | +25° C. | 2160 |
| Stoppering chamber pressure set point: 700 ± 50 mbar | | |

At the end of the lyophilization cycle the vials were discharged and some of them were analyzed with respect to the water content and the HPLC purity of the lyophilized product. The obtained data are summarized in the following table.

| | HP1 | Bendamustine purity | Water content (K.F.) |
|---|---|---|---|
| Vial n. 5 | 0.68% | 99.25% | 0.48% |
| Vial n. 10 | 0.60% | 99.28% | 0.62% |
| Vial n. 28 | 0.56% | 99.36% | 0.39% |
| Vial n. 46 | 0.50% | 99.39% | 0.46% |
| Vial n. 64 | 0.46% | 99.43% | 0.58% |
| Vial n. 82 | 0.47% | 99.39% | 0.49% |
| Vial n. 108 | 0.49% | 99.43% | 0.55% |
| Vial n. 118 | 0.48% | 99.44% | 0.88% |

The amounts of dimer trichloride and ethyl ester impurity evaluated by the used HPLC method (see example 1), which has a Limit of Detection of 0.02% and a Limit of Quantization of 0.03% for each of the mentioned impurities, were not detectable.

A vial of lyophilized product was analyzed to detect the content of the residual solvents by HSGC (Head Space Gas chromatography).

The analysis showed that the lyophilized product did not contain detectable residual solvents. The Limit of Detection of the used method was equal to 10 ppm.

Figure 3:
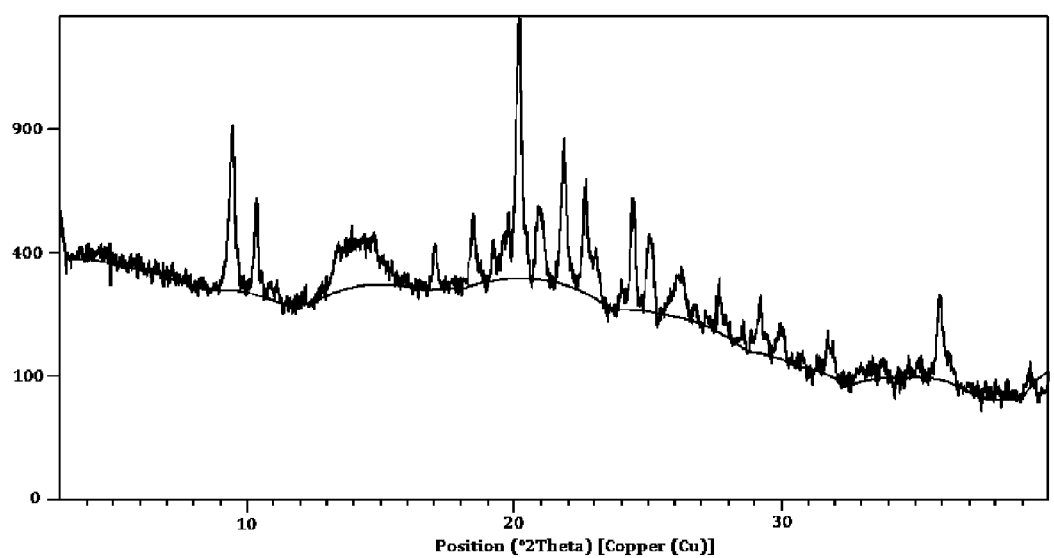
FIG. 3: PXRD of the product obtained in the example 6.

The PXRDs of the lyophilized product of a vial are reported in FIG. 3.

Some of the produced vials were reconstituted at room temperature with different amounts of water for injection observing a complete dissolution in the times reported in the following table

| Volume of added water for injectable solutions (ml) | Time for complete dissolution (sec) | Appearance of the reconstituted solution |
|---|---|---|
| 10 | 60 | Clear and colorless |
| 5 | 120 | Clear and colorless |
| 3.75 | 150 | Clear and colorless |
| 2.5 | 180 | Clear and colorless |

The vial n. 3 was kept for a month under the following conditions of stability: 25° C., 60% relative humidity, and re-analyzed after a month under such conditions obtaining the following result

| | HP1 | Bendamustine purity |
|---|---|---|
| Vial n. 3 | 0.63% | 99.28% |

The vial n. 4 was kept for a month under the following conditions of stability: 40° C., 75% relative humidity, and re-analyzed after a month under such conditions obtaining the following result

| | HP1 | Bendamustine purity |
|---|---|---|
| Vial n. 4 | 0.63% | 99.17% |

Example 7

Preparation of a Batch of Vials Containing 100 mg of Active Ingredient

| | Amount/vial | Mannitol:API ratio |
|---|---|---|
| API | 100 mg | 1.7 |
| Mannitol | 170 mg | |
| NaCl | — | |
| Pre-lyophilization solution volume | 30 ml | |

In a 2 liter reactor, equipped with thermo cryostat and mechanical stirring, cooled at 0° C. and coated with an aluminum sheet to shield the solution from light, a solution consisting of 10.2 g mannitol dissolved in 1.8 liter of water for injection were charged. Once the solution reached the thermal balance at 0-2° C., 6.03 g of bendamustine hydrochloride (having 99.8% purity and 0.11% HP1 impurity) were added. The complete dissolution of the solid was obtained after about 30 seconds. The mixture was kept under stirring at 0-2° C. for 2 hours, then filtered and charged on a vial filling system. 60 dark-glass 50H vials were filled with 30 ml of such solution, the vials were pre-capped with rubber stoppers for lyophilization and charged on a tray to be then transferred in a Minilyo Usifroid SMH45 lyophilizer with pre-cooled panels at 3° C.

A lyophilization cycle was applied according to the following table.

| Lyophilization Cycle Shelves T | Set point (° C.) | Set Time (min) |
|---|---|---|
| Loading with pre-cooled shelves | +3° C. | For vials loading |
| Freezing (shelves cooling) | −45° C. | 48 |
| Freezing (shelves holding) | −45° C. | 300 |
| Annealing (shelves heating) | (0.5°/min) −10° C. | 70 |
| Annealing (shelves holding) | −10° C. | 180 |
| Annealing (shelves cooling) | (0.5°/min) −45° C. | 70 |
| Annealing (shelves holding) | −45° C. | 240 |
| Primary drying (shelves heating) | −20° C. | 250 |
| Primary drying (shelves holding) | −20° C. | 5760 |
| Primary Drying chamber pressure set point: 100 microbar | | |
| Secondary drying (shelves heating) | +25° C. | 225 |
| Secondary drying (shelves holding) | +25° C. | 2450 |
| Stoppering chamber pressure set point: 700 ± 50 mbar | | |

At the end of the lyophilization cycle the vials were discharged and some of them were analyzed with respect to the water content and the HPLC purity (see example 1) of the lyophilized. The obtained data are summarized in the following table.

| | HP1 | Bendamustine purity | Water content (K.F.) |
|---|---|---|---|
| Vial n. 7 | 0.56% | 99.38% | 0.48% |
| Vial n. 13 | 0.49% | 99.45% | 0.62% |
| Vial n. 19 | 0.56% | 99.39% | 0.39% |
| Vial n. 25 | 0.55% | 99.39% | 0.46% |
| Vial n. 33 | 0.50% | 99.45% | 0.58% |
| Vial n. 44 | 0.48% | 99.48% | 0.49% |

The amounts of dimer trichloride and ethyl ester impurity evaluated with the used HPLC method which has a Limit of Detection of 0.02% and a Limit of Quantization of 0.03% for each of the mentioned impurities, were not detectable.

A vial of lyophilized product was analyzed to detect the content of the residual solvents by HSGC (Head Space Gas chromatography).

The analysis showed that the lyophilized product did not contain detectable residual solvents. The Limit of Detection of the used method was equal to 10 ppm.

Figure 4:
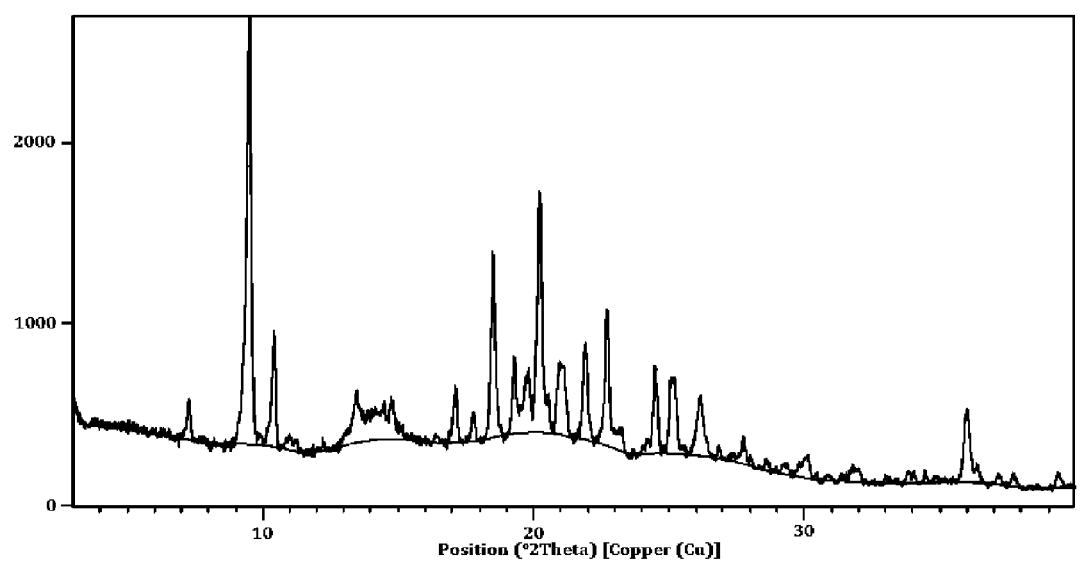
FIG. 4: PXRD of the product obtained in the example 7.

The PXRDs of the lyophilized product of a vial are reported in FIG. 4.

Some of the produced vials were reconstituted at room temperature with different amounts of water for injection observing a complete dissolution in the times reported in the following table

| Volume of added water for injectable solutions (ml) | Time for complete solubilization (sec) | Appearance of the reconstituted solution |
| --- | --- | --- |
| 40 | 60 | Clear and colorless |
| 20 | 120 | Clear and colorless |
| 15 | 150 | Clear and colorless |
| 10 | 180 | Clear and colorless |

The vial n. 35 was kept for a month under the following conditions of stability: 25° C., 60% relative humidity, and re-analyzed after a month under such conditions obtaining the following result

| | HP1 | Bendamustine purity |
| --- | --- | --- |
| Vial n. 35 | 0.46% | 99.47% |

The vial n. 34 was kept for a month under the following conditions of stability: 40° C., 75% relative humidity, and re-analyzed after a month under such conditions obtaining the following result

| | HP1 | Bendamustine purity |
| --- | --- | --- |
| Vial n. 34 | 0.50% | 99.42% |

Example 8

Preparation of a Lyophilized Formulation of Bendamustine Hydrochloride from Sole Water, without Sodium Chloride

| | Amount/vial | Mannitol:API ratio |
| --- | --- | --- |
| API | 100 mg | 1.2 |
| Mannitol | 120 mg | |
| NaCl | — | |
| Pre-lyophilization solution volume | 20 ml | |

In a 100 ml flask, 240.0 mg mannitol and 40 ml of MilliQ water were charged. The mixture was kept under stirring up to a complete dissolution of the solid and brought to a temperature of 4° C. 200.0 mg of bendamustine hydrochloride (having 99.8% purity and 0.11% HP1 impurity) were then added. After about 5 minutes a complete dissolution of the solid was observed. This solution was brought to a temperature from −1° C. to 2° C. and kept under such conditions for 3 hours after which it was filtered on a 0.22 μm filter, frozen at −20° C. and lyophilized under the conditions reported in example 2. A lyophilized product having a content of water of 2.30%, measured with the Karl Fischer method, HPLC purity 99.6% and HP1 impurity 0.35% was obtained.

A 22 mg portion of such lyophilized product was reconstituted with 2 ml of water for injection (API concentration=5 mg/ml) observing the complete dissolution of the product within a minute after the addition of the solvent.

A second 22 mg portion of the lyophilized product was reconstituted with 4 ml of water for injection (API concentration=2.5 mg/ml) observing the complete dissolution of the product within a minute after the addition of the solvent.

Example 9

Preparation of a Batch of Vials Containing 100 Mg of Active Ingredient

| | Amount/vial | Mannitol:API ratio |
| --- | --- | --- |
| API | 100 mg | 1.2 |
| Mannitol | 120 mg | |
| NaCl | — | |
| Pre-lyophilization solution volume | 20 ml | |

In a 2 liter reactor, equipped with thermo cryostat and mechanical stirring, cooled to 0° C. and coated with an aluminum sheet to shield the solution from light, a solution consisting of 7.2 g mannitol dissolved in 1.2 liter of water for injection was charged. Once the solution reached the thermal balance at 0-2° C., 6.03 g bendamustine hydrochloride (having 99.8% purity and 0.11% HP1 impurity) were added. The complete dissolution of the solid was obtained after about 30 seconds. The mixture was kept under stirring at 0-2° C. for 2 hours, then filtered and charged on a vial filling system. 60 dark-glass 50H vials were filled with 20 ml of such solution, the vials were pre-capped with rubber stoppers for lyophilization and charged on a tray to be then transferred in a Minilyo Usifroid SMH45 lyophilizer with pre-cooled panels at 3° C.

A lyophilization cycle was applied according to the following table.

| Lyophilization Cycle Shelves T | Set point (° C.) | Set Time (min) |
| --- | --- | --- |
| Loading with pre-cooled shelves | +3° C. | For vials loading |
| Freezing (shelves cooling) | −45° C. | 48 |
| Freezing (shelves holding) | −45° C. | 300 |
| Annealing (shelves heating) | (0.5°/min) −10° C. | 70 |
| Annealing (shelves holding) | −10° C. | 180 |
| Annealing (shelves cooling) | (0.5°/min) −45° C. | 70 |
| Annealing (shelves holding) | −45° C. | 240 |
| Primary drying (shelves heating) | −20° C. | 250 |
| Primary drying (shelves holding) | −20° C. | 5760 |
| Primary Drying chamber pressure set point: 100 microbar | | |
| Secondary drying (shelves heating) | +25° C. | 225 |
| Secondary drying (shelves holding) | +25° C. | 2450 |
| Stoppering chamber pressure set point: 700 ± 50 mbar | | |

At the end of the lyophilization cycle the vials were discharged and some of them were analyzed with respect to the water content and the HPLC purity of the lyophilized product. The obtained data are summarized in the following table.

| | HP1 | Bendamustine purity | Water content (K.F.) |
|---|---|---|---|
| Vial n. 4 | 0.52% | 99.37% | 0.54% |
| Vial n. 10 | 0.49% | 99.40% | 0.47% |
| Vial n. 20 | 0.48% | 99.43% | 0.40% |
| Vial n. 30 | 0.46% | 99.44% | 0.35% |
| Vial n. 40 | 0.46% | 99.45% | 0.40% |

The amounts of dimer trichloride and ethyl ester impurity evaluated with the used HPLC method (see example 1) which has a Limit of Detection of 0.02% and a Limit of Quantization of 0.03% for each of the mentioned impurities, was not detectable.

A vial of lyophilized product was analyzed to detect the content of the residual solvents by HSGC (Head Space Gas chromatography).

The analysis showed that the lyophilized product did not contain detectable residual solvents. The Limit of Detection of the used method was equal to 10 ppm.

Figure 5:
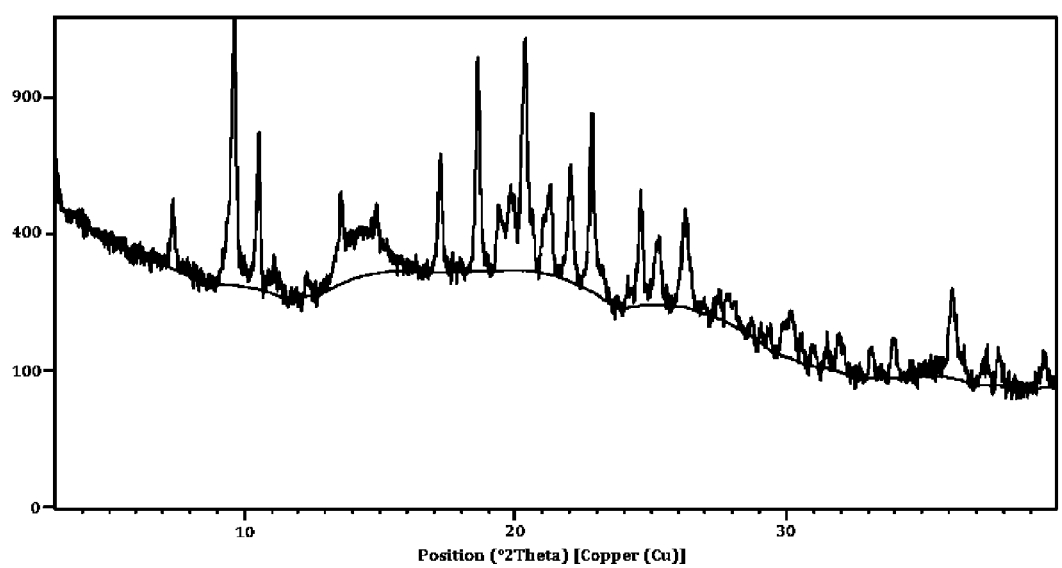
FIG. 5: PXRD of the product obtained in the example 9.

The PXRDs of the lyophilized product of a vial are reported in FIG. 5.

Some of the produced vials were reconstituted at room temperature with different amounts of water for injection, observing the complete dissolution in the times reported in the following table.

| Volume of added water for injectable solutions (ml) | Time for complete solubilization (sec) | Appearance of the reconstructed solution |
|---|---|---|
| 40 | 60 | Clear and colorless |
| 20 | 120 | Clear and colorless |
| 15 | 150 | Clear and colorless |
| 10 | 180 | Clear and colorless |

Example 10

Preparation of an Industrial Batch of Vials Containing 100 mg of Active Ingredient

| | Amount/vial | Mannitol:API ratio |
|---|---|---|
| API | 100 mg | 1.2 |
| Mannitol | 120 mg | |
| NaCl | — | |
| Pre-lyophilization solution volume | 20 ml | |

1800 amber 50 ml vials were prepared in a sterilization tunnel, ready to be filled. In a pre-dissolutor, equipped with cooling jacket, 21 kg of water for injection were charged. The water was brought to a temperature of 0-2° C. 216 g mannitol for injectable preparations were added and the mixture was kept under stirring for 10 minutes, until complete dissolution. From a glass container, 180 g of bendamustine hydrochloride were then added, making a rinse of the container with 2×700 and 1×600 ml of water for injection kept at 2° C. The content of the pre-dissolutor was transferred into a dissolutor with a peristaltic pump, washing the pre-dissolutor with 3 liters of water for injection. The final weight of the mixture contained in the dissolutor was brought to 36.07 kg by adding water for injection kept at 0-2° C. The mixture was kept under stirring at 0-2° C. until complete dissolution of the product (about 30 minutes). The appearance of the solution was checked, then the solution was filtered on a sterilization filter Millipak 200 porosity 0.22 micron. The filtered solution was transferred in a jacketed collector with circulating refrigerant fluid keeping the solution at 0-2° C. Part of the solution was collected in order to verify the absence of bacterial contamination and pyrogens. The solution was transferred from the collector to the line of distribution where, by using calibrated dispensing needles, the vials were filled in with 20 ml of solution each. Every 15 minutes the weight of the solution contained in each vial, was verified. Each vial was equipped automatically with a stopper and moved in the loading zone of the lyophilization trays, where it was ordered. At the end of the filling of each tray, this was placed in a lyophilizer with plates kept at 2° C. Once the loading of all trays was completed, temperature probes were placed in each tray, the lyophilizer was closed and the sequence of the lyophilization cycle consisting of the following phases was started.

| Phase | Temperature of the plates | Time (h) |
|---|---|---|
| Plate loading | +2° C. | — |
| Freezing | −45° C. | 1:40 |
| Maintaining | −45° C. | 3:00 |
| Annealing | −10° C. | 1:20 |
| Annealing | −10° C. | 3:00 |
| Annealing | −45° C. | 1:16 |
| Annealing | −45° C. | 3:00 |
| Primary drying | −20° C. | 4:10 |
| Primary drying | −20° C. | 48:00 |
| Secondary drying | +25° C. | 3:45 |
| Secondary drying | +25° C. | 12:00 |
| Secondary drying | +35° C. | 0:10 |
| Secondary drying | +35° C. | 10:00 |
| Secondary drying | +25° C. | 0:10 |
| Secondary drying | +25° C. | 12:00 |

At the end of the process all the vials were closed, sealed and collected in suitable trays for storage.

Five samples of vials from different trays were sent to the analysis for the control of water content and HPLC purity (see example 1).

The obtained results are the following:

| | HP1 | Bendamustine purity | Water content (K.F.) |
|---|---|---|---|
| Vial n. 1 | 0.49 | 99.36 | — |
| Vial n. 2 | 0.48 | 99.37 | — |
| Vial n. 3 | 0.47 | 99.39 | — |
| Vial n. 4 | — | — | 0.42% |
| Vial n. 5 | — | — | 0.41% |
| Vial n. 6 | — | — | 0.38% |

A vial of lyophilized product was analyzed to detect the content of residual solvents by HSGC (Head Space Gas Chromotography).

The analysis showed that the lyophilized product did not contain detectable residual solvents. The Limit of Detection of the used method was equal to 10 ppm.

One of the produced vials was reconstituted at room temperature with 20 ml of water for injection, observing the complete dissolution within 60 seconds.

Figure 6:
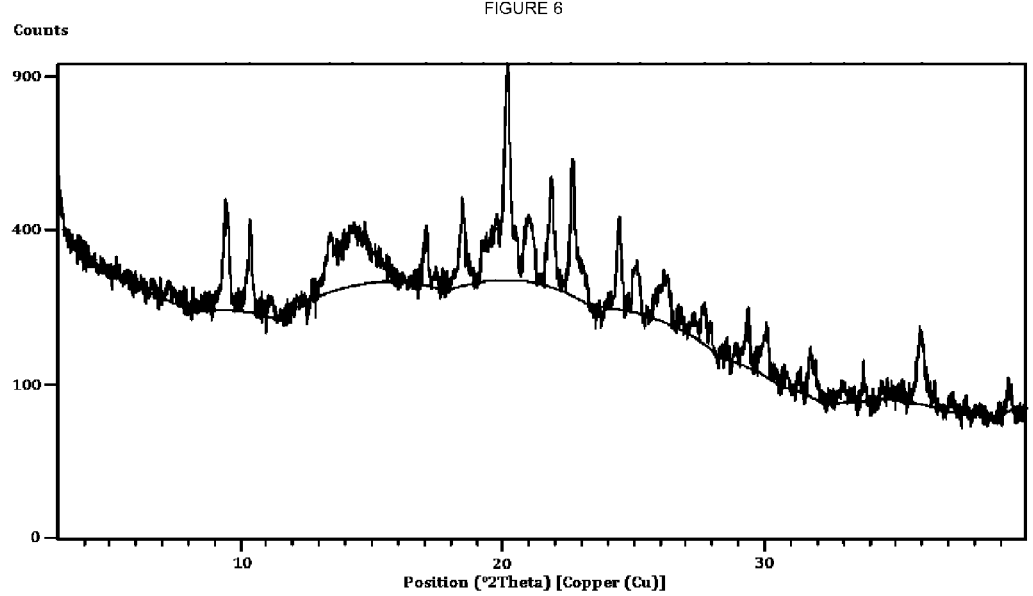
FIG. 6: PXRD of the product obtained in the example 10.

The PXRDs of the content of a bottle vial are reported in FIG. 6.

Example 11

Determination of the Residual Solvent Content in the Commercial Products TREANDA® and LEVACT®

Three samples of the commercial products TREANDA® and LEVACT® were analyzed by HSGC (Head Space Gas Chromotography) to determine their content of residual solvents. The used method was the same used in examples 6 and 7.

The obtained results are reported in the following table

| Product | Dosage | Lot n. | t-BuOH (ppm) | EtOH (ppm) |
|---|---|---|---|---|
| TREANDA® | 100 mg | TA31510 | 1800 | — |
| LEVACT® | 100 mg | 106662 | — | 253 |
| LEVACT® | 25 mg | 99278 | — | 236 |

Example 12

Analysis of Purity of Commercial Samples of TREANDA® and LEVACT®

Two vials of the commercial products TREANDA® and LEVACT® were analysed to determine HPLC purity, with the same method described in Example 1.

The results are reported in the following table.

| | Lot. N. | Bendamustine | HP1 imp. | Dimer trichloride imp. | Ethyl ester imp. |
|---|---|---|---|---|---|
| LEVACT® 25 mg | 99278 | 98.15% | 1.50% | 0.20% | 0.15% |
| LEVACT® 100 mg | 106662 | 98.83% | 0.90% | 0.18% | 0.17% |
| TREANDA® 100 mg | TA31510 | 99.24% | 0.23% | 0.17% | 0.18% |

Example 13

Preparation of a Batch of Vials Containing 100 mg of Active Ingredient

| | Amount/vial | Mannitol:API ratio |
|---|---|---|
| API | 100 mg | 1.0 |
| Mannitol | 100 mg | |
| Na Cl | — | |
| Pre-lyophilization solution volume | 20 ml | |

In a 2 liter reactor, equipped with thermo cryostat and mechanical stirring, cooled to 0° C. and coated with an aluminum sheet to shield the solution from light, a solution consisting of 6.0 g di mannitol dissolved in 1.2 liter of water for injection was charged. Once the solution reached the thermal balance at 0-2° C., 6.03 g bendamustine hydrochloride (having 99.8% purity and 0.11% HP1 impurity) were added. The complete dissolution of the solid was obtained after about 30 seconds. The mixture was kept under stirring at 0-2° C. for 2 hours, then filtered and charged on a vial filling system. 60 dark-glass 50H vials were filled with 20 ml of such solution, the vials were pre-capped with rubber stoppers for lyophilization and charged on a tray to be then transferred in a Minilyo Usifroid SMH45 lyophilizer with pre-cooled panels at 3° C.

A lyophilization cycle was applied according to the following table.

| Lyophilization Cycle Shelves T | Set point (° C.) | Set Time (min) |
|---|---|---|
| Loading with pre-cooled shelves | +3° C. | For vials loading |
| Freezing (shelves cooling) | −45° C. | 48 |
| Freezing (shelves holding) | −45° C. | 300 |
| Annealing (shelves heating) | (0.5°/min) −10° C. | 70 |
| Annealing (shelves holding) | −10° C. | 180 |
| Annealing (shelves cooling) | (0.5°/min) −45° C. | 70 |
| Annealing (shelves holding) | −45° C. | 240 |
| Primary drying (shelves heating) | −20° C. | 250 |
| Primary drying (shelves holding) | −20° C. | 5760 |
| Primary Drying chamber pressure set point: 100 microbar | | |
| Secondary drying (shelves heating) | +25° C. | 225 |
| Secondary drying (shelves holding) | +25° C. | 2450 |
| Stoppering chamber pressure set point: 700 ± 50 mbar | | |

At the end of the lyophilization cycle the vials were closed, sealed and discharged and some of them were analyzed with respect to the water content and the HPLC purity of the lyophilized product. The obtained data are summarized in the following table.

| | HP1 | Bendamustine purity | Water content (K.F.) |
|---|---|---|---|
| Vial N° 5 | 0.52% | 99.38% | 0.55% |
| Vial N° 11 | | | 0.47% |

The amounts of dimer trichloride and ethyl ester impurity evaluated with the used HPLC method (see example 1) which has a Limit of Detection of 0.02% and a Limit of Quantization of 0.03% for each of the mentioned impurities, was not detectable.

A vial of lyophilized product was analyzed to detect the content of the residual solvents by HSGC (Head Space Gas chromatography).

The analysis showed that the lyophilized product did not contain detectable residual solvents. The Limit of Detection of the used method was equal to 10 ppm.

Figure 7:
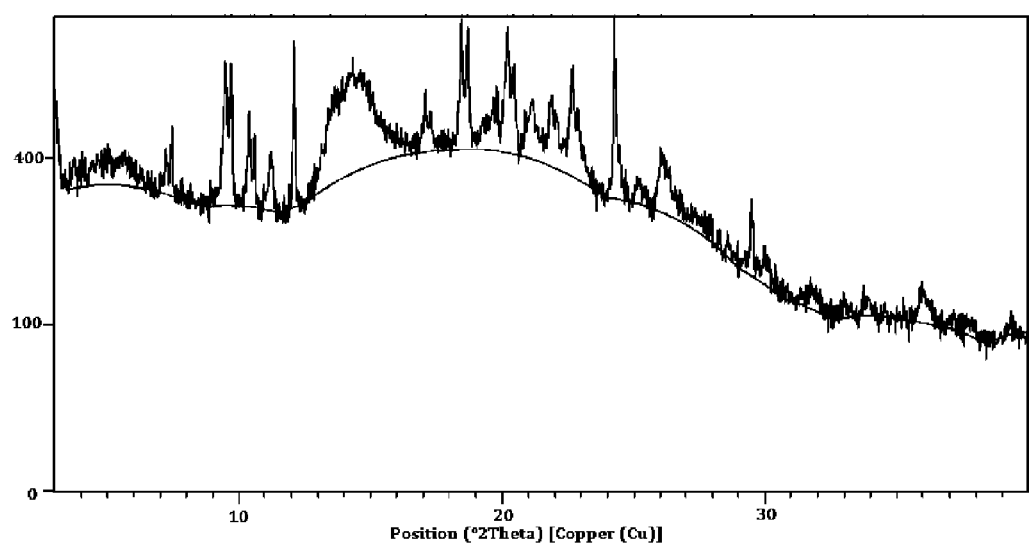
FIG. 7: PXRD of the product obtained in the example 13.
Figure 8:
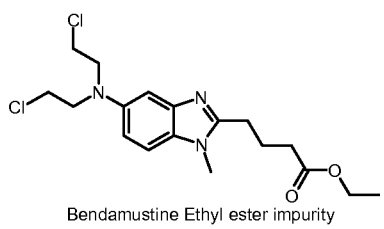
FIG. 8 shows the Bendamustine Impurities.
Figure 8:
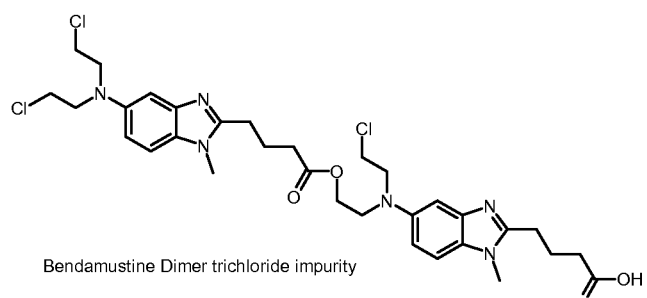
Figure 8:
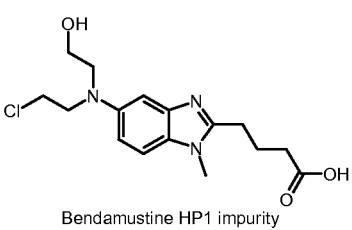
Figure 8:
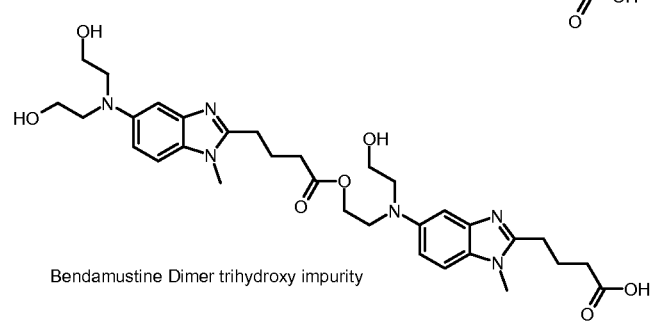

The PXRDs of the lyophilized product of a vial are reported in FIG. 7.

One vial was reconstituted at room temperature with 20 ml of water for injection, observing complete dissolution within one minute.

The invention claimed is:

1. Process to obtain lyophilized bendamustine hydrochloride free from organic solvents and with a purity of at least 99%, said process comprising
    dissolving bendamustine hydrochloride in an aqueous solution comprising at least one excipient to obtain a pre-lyophilized solution, wherein the ratio bendamustine hydrochloride to excipients is 10:12 and
    lyophilizing said pre-lyophilized solution,
    thereby obtaining said lyophilized bendamustine hydrochloride free from organic solvents and with a purity of at least 99%.

2. The process of claim 1, wherein said excipient is selected from the group consisting of mannitol, lactose and sucrose or mixtures thereof.

3. The process of claim 2, wherein said excipient is mannitol.

4. The process of claim 1, wherein the bendamustine hydrochloride is at a concentration of between about 2.0 and 5.5 mg/ml.

5. The process of claim 2, wherein said excipient is at a concentration of between about 3.0 to about 8.5 mg/ml.

6. The process of claim 1, wherein said pre-lyophilized solution is maintained at a temperature of less than about 5° C.

7. The process of claim 1, comprising obtaining a first solution of said bendamustine hydrochloride in water and adding said first solution to the aqueous solution comprising said at least one excipient.

8. The process of claim 1 wherein the aqueous solution comprising the at least one excipient comprises NaCl.

9. The process of claim 8 wherein said NaCl is at a concentration of between about 0.1% to 1% w/v.

10. A lyophilized formulation of bendamustine hydrochloride devoid of residual organic solvents and having a HPLC purity of at least 99%, wherein the ratio bendamustine hydrochloride to excipient is 10:12.

11. The lyophilized formulation of claim 10, having a HPLC purity of at least 99.5%, wherein the ratio bendamustine hydrochloride to excipient is 10:12.

12. An injectable solution obtained by reconstituting in water the formulation of claim 10 and comprising bendamustine hydrochloride at a concentration of 5 mg/ml.

13. An injectable solution obtained by reconstituting in water the formulation of claim 10 and comprising bendamustine hydrochloride at a concentration of 2.5 mg/ml.

14. The injectable solution of claim 12, wherein the lyophilized formulation of bendamustine hydrochloride is reconstituted in 20 ml.

15. The injectable solution of claim 13, wherein the lyophilized formulation of bendamustine hydrochloride is reconstituted in 40 ml.

* * * * *